United States Patent [19]

König et al.

[11] Patent Number: 5,434,138
[45] Date of Patent: Jul. 18, 1995

[54] GONADOLIBERIN ANTAGONISTS

[75] Inventors: Wolfgang König, Hofheim am Taunus; Jürgen Sandow, Königstein/Taunus; Cenek Kolar, Marburg, all of Germany

[73] Assignee: Hoechst Aktiengesellschaft, Frankfurt am Main, Germany

[21] Appl. No.: 151,056

[22] Filed: Nov. 12, 1993

Related U.S. Application Data

[63] Continuation of Ser. No. 739,233, Aug. 1, 1991, abandoned.

[30] Foreign Application Priority Data

Aug. 4, 1990 [DE] Germany .................. 40 24 779.1

[51] Int. Cl.⁶ .................. A61K 38/00; C07K 7/00; C07K 7/23
[52] U.S. Cl. .................. 514/15; 530/313; 530/328
[58] Field of Search .................. 530/328, 313; 514/15

[56] References Cited

U.S. PATENT DOCUMENTS

| | | | |
|---|---|---|---|
| 4,229,438 | 10/1980 | Fujino et al. | 530/328 |
| 4,661,472 | 4/1987 | Rivier et al. | 530/328 |
| 4,801,577 | 1/1989 | Nestor, Jr. et al. | 530/328 |
| 5,073,624 | 12/1991 | Coy et al. | 530/328 |
| 5,091,367 | 2/1992 | König et al. | 530/328 |
| 5,110,904 | 5/1992 | Haviv et al. | 530/328 |

FOREIGN PATENT DOCUMENTS

79459/87   1/1990   Australia .
0263521    4/1988   European Pat. Off. .
2218102   11/1989   United Kingdom .

OTHER PUBLICATIONS

Folkers et al, Biochem and Biophys Res. Comm. vol. 123, No. 3, pp. 1221–1226, 1984.

Ljungqvist et al., "Design, Synthesis and Bioassays of Antagonists of LHRH Which Have High Antiovulatory Activity and Release Negligible Histamine", Biochemical and Biophysical Research Communications, 148, 849–856 (1987).

European Search Report.

Primary Examiner—Jill Warden
Assistant Examiner—S. G. Marshall
Attorney, Agent, or Firm—Finnegan, Henderson, Farabow, Garrett & Dunner

[57] ABSTRACT

Peptides of the formula $$\overset{1}{X}-\overset{2}{A}-\overset{3}{B}-\overset{4}{C}-\overset{5}{Ser}-\overset{6}{D}-\overset{7}{E}-\overset{8}{F}-\overset{9}{G}-\overset{10}{Pro}-H$$

in which X is alkanoyl, A is optionally substituted D-Nal(2), D-Phe or D-Trp, B is optionally substituted D-Phe, C is D-Pal(3) or optionally substituted D-Phe or D-Trp, and D is Tyr or His, E is D-Ser ($R^1$), F is Leu, Trp or Phe, G is L-Ser($R^1$), H is Gly-$NH_2$, D-Ala-$NH_2$ or Azagly-$NH_2$ and $R^1$ is a glycosyl radical. These peptides have an inhibitory effect on the formation of the gonadotropins lutropin and follitropin and thus also on the synthesis of testo-sterone and estrogen. A process for the preparation of these peptides is described.

4 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Gly Pro Arg Leu Gly Tyr Ser Trp His Xaa
 1               5                   10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Gly Pro Gln Leu Gly Tyr Ser Trp His Xaa
 1               5                   10
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Gly Pro Tyr Trp Gly His Ser Trp His Xaa
 1               5                   10
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Gly Pro Leu Trp Gly Tyr Ser Trp His Xaa
 1               5                   10
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide (xi) SEQUENCE DESCRIPTION: SEQ ID NO:5:

Gly Pro Lys Trp Glu Leu Ser Tyr His Xaa
1               5                   10

GONADOLIBERIN ANTAGONISTS

This application is a continuation of application Ser. No. 07/739,233, filed Aug. 1, 1991, now abandoned.

Naturally occurring gonadoliberins (Gn-RH) of various species are decapeptides of the following structures:

| | |
|---|---|
| h-, p-, o- | Pgl—His—Trp—Ser—Tyr—Gly—Leu—Arg—Pro—Gly—NH$_2$ |
| g-Gn-RH-I | Pgl—His—Trp—Ser—Tyr—Gly—Leu—Gln—Pro—Gly—NH$_2$ |
| g-Gn-RH-II | Pgl—His—Trp—Ser—His—Gly—Trp—Tyr—Pro—Gly—NH$_2$ |
| sa-Gn-RH | Pgl—His—Trp—Ser—Tyr—Gly—Trp—Leu—Pro—Gly—NH$_2$ |
| pe-Gn-RH | Pgl—His—Tyr—Ser—Leu—Glu—Trp—Lys—Pro—Gly—NH$_2$ |

[h-(human), p-(pig), o-(sheep): Biochem. Biophys. Res. Commun. 43 (1971) 1334; g-(chicken I): South Africa J. Science 78 (1982) 124; g-(chicken II): Proc. Natl. Acad. Sci. USA 81 (1984) 3874; sa-(salmon): Proc. Natl. Acad. Sci. USA 80 (1983) 2794; pe-(lamprey): J. Biol. Chem. 261 (1986) 4812–4819].

Gn-RH is in mammals mainly formed in the hypothalamus and brings about secretion of lutropin (LH) and follitropin (FSH) in the pituitary.

Competitive antagonists of Gn-RH inhibit, via blockade of Gn-RH receptors, the formation of LH and FSH and thus also the synthesis of estrogen in female animals or women or testosterone in male animals or men. Numerous Gn-RH antagonists have already been described in the literature [J. J. Nestor, Jr. et al. In: LH-RH and its analogues (F. Labrie et al., eds.) Elsevier Science Publishers B. V. 1984. pp. 24–35; A. S. Dutta, Drugs of the Future 13 (1988) 761–787], most of which contain a basic amino acid in position 6. This basic charge in position 6 makes the peptides more soluble in water. An adverse concomitant phenomenon of this basic group is, however, a histamine-secreting action. "Nal-Glu" in which the Arg in position 5 has been displaced and there is D-4-p-methoxybenzoyl-2-aminobutyric acid in position 6 has a greatly reduced histamine secretion [A. Phillips et al., Life Sci. 41 (1987) 2017–2022]. Less basic substitutions in position 6, such as, for example, D-nicotinoyllysine [K. Folkers et al., Z. Naturforsch. 42b (1987) 101–106; A. Ljungqvist et al., Biochem. Biophys. Res. Commun. 148 (1987) 849–856], D-citrulline or D-homocitrulline [S. Bajusz et al. Proc. Natl. Acad. Sci. USA 85 (1988) 1637–1641] likewise reduce the histamine release.

In EP-A 263 521 (HOE 86/F 253), both Gn-RH agonists and Gn-RH antagonists with beneficial properties were obtained by substitution with glycosylated sugars. It was possible, on the one hand, to increase the solubility in water and, on the other hand, to reduce the anaphylactic action which was particularly observable with Gn-RH antagonists.

It was possible to reduce the histamine release while retaining the antagonistic action by replacing the arginine in position 8 by other basic amino acids such as Nε-isopropyl-L-lysine [A. Ljungqvist et al., Biochem. Biophys. Res. Commun. 148 (1987) 849–856] or Ng,Ng'-diethyl-L-homoarginine [C.-H. Less et al. Life Sci. 45 (1989) 697–702]. To date it has been assumed that the basic charge in position 8 plays an important part in the receptor binding of Gn-RH in mammals (E. Hazum and P. M. Conn, Endocrine Reviews 9 (1988) 379–386).

The object of further reducing the histamine release while retaining the antagonistic action is achieved, surprisingly, by exchanging, compared with the known Gn-RH derivatives containing a basic charge in the 8 position, this position by glycosylated L-serine.

The invention relates to peptides of the formula I

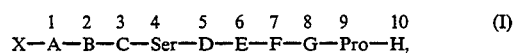

$$\begin{array}{cccccccccc} 1 & 2 & 3 & 4 & 5 & 6 & 7 & 8 & 9 & 10 \\ X\text{—}A\text{—}B\text{—}C\text{—}\text{Ser}\text{—}D\text{—}E\text{—}F\text{—}G\text{—}\text{Pro}\text{—}H, \end{array} \quad (I)$$

in which

X is C$_2$–C$_8$-alkanoyl;

A is D-Nal (2), D-Phe or D-Trp, where the aromatic ring can optionally be substituted by one or two identical or different radicals from the series comprising bromine, chlorine, fluorine, nitro, C$_1$–C$_4$-alkyl, especially methyl, and C$_1$–C$_4$-alkoxy, especially methoxy;

B is D-Phe which can optionally be substituted by one or two identical or different radicals from the series comprising bromine, chlorine, fluorine, nitro, amino, C$_1$–C$_4$-alkyl, especially methyl, and C$_1$–C$_4$-alkoxy, especially methoxy;

C is D-Pal (3), D-Phe or D-Trp, where the aromatic ring of D-Phe and D-Trp can optionally be substituted by one or two identical or different radicals from the series comprising bromine, chlorine, fluorine, nitro, C$_1$–C$_4$-alkyl, especially methyl, and C$_1$–C$_4$-alkoxy, especially methoxy;

D is Tyr or His;

E is D-Ser(R$^1$);

F is Leu, Trp or Phe;

G is L-Ser(R$^1$);

H is Gly-NH$_2$, D-Ala-NH$_2$ or Azagly-NH$_2$;

R$^1$ is a glycosyl radical; and the physiologically tolerated salts thereof.

Gn-RH antagonists of the formula I in which

X is acetyl;

A is D-Nal(2);

B is D-Phe(p-Cl);

C is D-Pal(3) or D-Trp;

D is Tyr;

E is D-Ser(R$^1$);

F is Leu;

G is L-Ser (R$^1$); H is D-Ala-NH$_2$ or Azagly-NH$_2$, and the physiologically tolerated salts thereof, are preferred.

Alkyl or alkoxy can be straight-chain or branched.

R$^1$ is preferably a glycosyl radical derived from a glycopyranose, glycofuranose or an oligosaccharide. The glycosyl radicals can be linked both α- and β-glycosidically to the serine residue.

R$^1$ can be, for example, a glucofuranosyl or glucopyranosyl radical which is derived from naturally occurring aldotetroses, aldopentoses, oligosaccharides such as di- and trisaccharides, and stereoisomers thereof.

These glycosyl radicals $R^1$ are derived, in particular, from natural D- or L-monosaccharides which occur in microorganisms, plants, animals or humans, such as ribose (Rib), arabinose (Ara), xylose (Xyl), lyxose (Lyx), allose (All), altrose (Alr), glucose (Glc), mannose (Man), gulose (Gul), idose (Ido), galactose (Gal), talose (Tal), erythrose (Ery), threose (Thr), psicose (Psi), fructose (Fru), sorbose (Sor), tagatose (Tag), xylulose (Xyu), fucose (Fuc), rhamnose (Rha), olivose (Oli), oliose (Olo), mycarose (Myc), rhodosamine (RN), N-acetylglucosamine (GlcNAc), N-acetylgalactosamine (GalNAc), N-acetylmannosamine (ManNAc) or disaccharides such as maltose (Mal), lactose (Lac), cellobiose (Cel), gentiobiose (Gen), N-acetyllactosamine (LacNAc), chitobiose (Chit), $\beta$-galactopyranosyl-(1,3)- or -(1,4)-N-acetylglucosamine, and the synthetic derivatives thereof, such as 2-deoxy-, 2-amino-, 2-acetamido- or 2-halogeno-, preferably bromo- and iodo-sugars. Unless otherwise indicated, the amino acids without a stereodescriptor represent L-amino acids. By physiologically tolerated salts are meant, in particular, those with inorganic acids such as HCl, HBr, $H_2SO_4$, $H_3PO_4$, or organic acids such as acetic acid, maleic acid, fumaric acid, tartaric acid, citric acid.

The invention furthermore relates to a process for the preparation of the peptides of the formula I, which comprises condensing a fragment with an N-terminal free amino group with a fragment with a C-terminal free carboxyl group, eliminating one or more protective groups which may have been temporarily introduced to protect functional groups, and converting the peptide obtained in this way where appropriate into its physiologically tolerated salt.

The selection of the protective groups and the synthesis strategy is determined by the nature and configuration of the amino acids and the nature of the coupling conditions. Suitable methods are described, for example, in EP-A 263 521, or are general methods of peptide chemistry (Houben-Weyl, Methoden der Organischen Chemie [Methods of organic chemistry] Volume 125) by stepwise synthesis from the C-terminal end or segment condensation. The synthesis of the serine glycosides is described in EP-A 263 521.

In order to keep the racemization which is possible in the segment condensation as low as possible, it is preferable to use in this connection dicyclohexyl-carbodiimide (DCC) with the addition of 3-hydroxy-4-oxo-3,4-dihydro-1,2,3-benzotriazine (HOObt). The amino-protective groups which are preferably used are the Z radical which can be eliminated by catalytic hydrogenation or the Fmoc radical which can be eliminated by secondary amines.

A segment coupling in accordance with the scheme (1–5)+(6–10)→(1–10)

has proven particularly beneficial.

The synthesis is illustrated by the following reaction scheme.

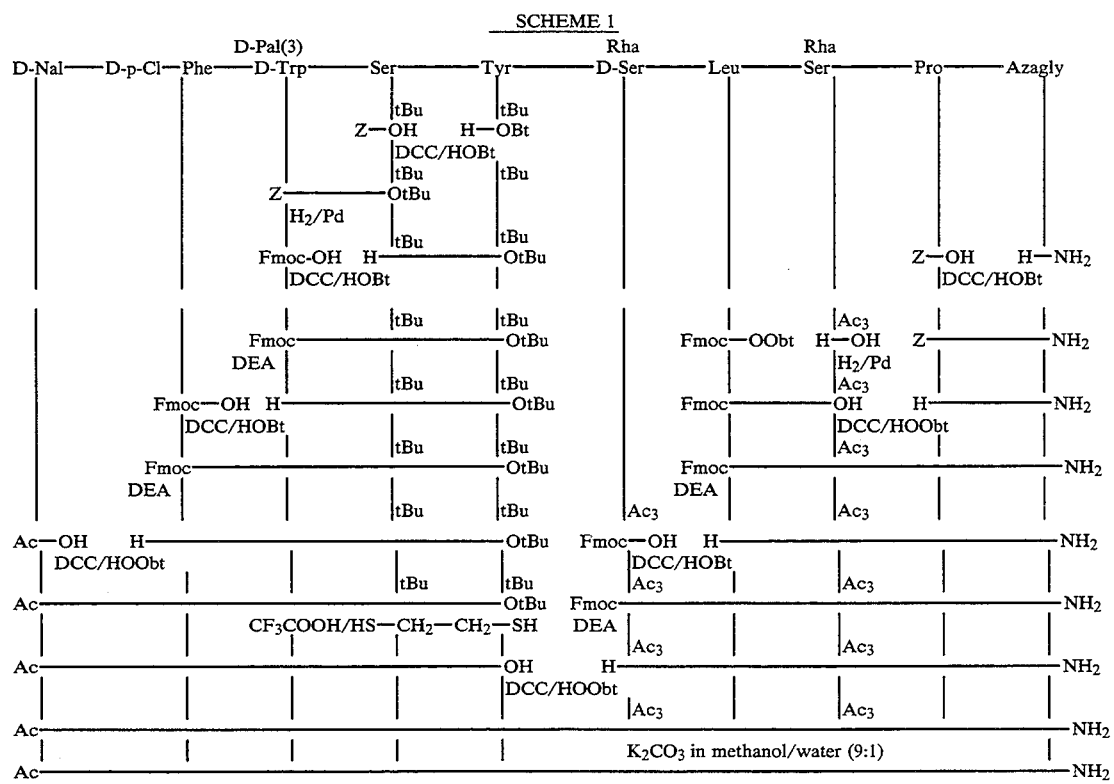

The Gn-RH antagonists according to the invention act to inhibit the formation of the gonadotropins lutropin and follitropin and thus also the synthesis of testosterone and estrogen. They can be employed like high-dose Gn-RH agonists in gonadotropin- and steroid-dependent disorders, as described, for example, in EP-A 263 521, and in birth control; Pubertas praecox; in the treatment of testosterone- and estrogen-dependent tumors such as, for example, prostate cancer and breast cancer; in the treatment of endometriosis and myomas. Furthermore, the peptides according to the invention protect the gonads from X rays. However, the advantage of the antagonists compared with the high-dose agonists is that the initial stimulation phase of the agonists is avoided.

The Gn-RH antagonists according to the invention can be administered parenterally, intranasally or as implants, as described, for example, in EP-A 263 521. The preferred forms of administration in humans are intranasal administration or the use of implants.

A metered atomizer is used to spray, via a spray nozzle, about 0.02–0.2 ml of a buffer solution in which the required amount of the active substance is dissolved into the nose. On parenteral administration, the dosages can be reduced by about one power of ten by comparison with the intranasal dose.

The antagonists according to the invention are administered intranasally in doses of 1–10 mg for human adults. The single dose in implants is about 5–50 mg for a period of 4–8 weeks in each case. 0.1–1 mg/day suffices for parenteral administration.

The peptides according to the invention have been tested for an atrophic effect on androgen-dependent organs and for an LH- and testosterone-lowering effect in serum and blood of male rats by continuous infusion (MINIPUMPS). The ovulation-inhibiting effect has been tested on female rats. The histamine release was checked using rat peritoneal mast cells.

Testosterone-lowering effect:

The testosterone-lowering effect was tested on male rats during subcutaneous infusion for 7 days. The biological effect on androgen-dependent organs and serum testosterone was recorded. The test compounds were administered by subcutaneous infusion using minipumps at a rate of 30–50 µg/day for 7 days. The test compounds were dissolved in sterile 5 % strength mannitol solution. The minipumps were implanted subcutaneously in the region of the back under anesthesia and aseptic conditions.

Serum testosterone was extracted with diethyl ether and determined by a specific RIA.

Testosterone-lowering effect on infusion by minipumps

| Example | Dose per day (µg/24 h/rat) |
| --- | --- |
| 1 | 120 |
| 2 | 120 |
| 3 | 120 |
| 4 | 60 |
| 5 | 60 |

Ovulation-inhibiting effect:

The ovulation-inhibiting effect was tested in immature female rats which had been pretreated with PMSG (pregnant mare serum gonadotropin) in order to induce follicle maturation, Spontaneous ovulation was prevented by barbiturate (phenobarbital). A test dose of 800 ng of LHRH was injected subcutaneously 2 hours after the antagonists. The test substances were injected subcutaneously dissolved in 5% strength mannitol solution. The next day the Fallopian tubes were dissected out and stained with Patent Blue, and the tubular oocytes were counted under a microscope. The dose for an ovulation-inhibiting effect (ED 100) was determined for all the antagonists.

Rat antiovulation assay

| Example | Ovulation-inhibiting dose (ng per rat s.c.) |
| --- | --- |
| 1 | 120 |
| 2 | 256 |
| 3 | 512 |
| 4 | 64 |
| 5 | 64 |

Histamine release:

a) Preparation of the peritoneal cell suspension

Wistar rats were sacrificed by decapitation. 50 ml of a 0.9% strength NaCl solution were injected into the abdominal cavity and, after gentle massage, the abdominal wall was opened. The fluid, which contains the peritoneal cells, was aspirated using a Pasteur pipette and then centrifuged. The pelleted cells were resuspended and, after testing viability, diluted to $10^6$ mast cells/ml.

b) Treatment of the mast cells

150 µl of the dissolved gonadoliberin antagonist were added to a suspension of $10^5$ mast cells in 150 µl of 0.9 % strength NaCl solution. After incubation at 37° C. for 30 minutes, the test tubes were centrifuged and the supernatant was removed. The LHRH antagonist Ac-D-Nal-D-p-Cl-D-Phe-D-Trp-Ser-Tyr-D-Ser(Rha)-Leu-Arg-Pro-Azagly-$NH_2$, known to be a compound which induces histamine release by mast cells, was used as comparison substance. To determine the total histamine release (100%), the mast cell suspensions were rapidly boiled over a Bunsen burner.

c) HPLC determination of the histamine level

A modified form of the methods described by Skofitsch et al. (J. Chromatography, 226, 53–59, 1981) and Siraganian and Hook (in Manual of Clinical Laboratory Immunology; eds: Rose et al. American Society of Microbiology, Washington D.C., pages 675, 1986) was used. Briefly summarized, 100 µl of a 1N NaOH and 100 µl of phthalaldehyde were added to 250 µl of supernatant and shaken vigorously. After a reaction time of 2 minutes, the fluorophore was converted into a more strongly fluorescent and stable product by acidification with 50 µl of 3N HCl. 10 µl of the supernatant were injected into the Chromspher C8 column (Chrompak FRW) of the HPLC system. This system comprises an SP 8100 chromatograph (Spectra Physics) and an SP 4270 integrator (Spectra Physics) and an LS-1 fluorescence detector (Perkin Elmer). The fluorescence was recorded at the wavelengths of 360 nm excitation and 450 nm emission.

Histamine release from peritoneal mast cells (µl/ml)

| (Results are given in percentages relative to the total values of the histamine release caused by the lysis of the mast cells on boiling) | | | | | |
| --- | --- | --- | --- | --- | --- |
| Example | 100 | 10 | 1 | 0.1 | 0.01 |
| 1 | −8.61 | −5.37 | −2.16 | 2.82 | 0.33 |
| 2 | 0.0 | 0.9 | 3.7 | 4.6 | 2.5 |
| 5 | 3.8 | 0.3 | 0.9 | 2.4 | 1.9 |
| Comparison substance | 107.6 | 92.4 | 15.3 | 2.1 | 2.6 |

Other abbreviations used:

| | |
| --- | --- |
| DCC | dicyclohexylcarbodiimide |
| DEA | diethylamine |
| HOBT | 1-hydroxybenzotriazole |

| | |
|---|---|
| MTB ether | methyl tert.-butyl ether |
| NaI | 3-(2-naphthyl)-alanine |
| Pal | 3-(3-pyridyl)-alanine |

The following examples illustrate the present invention.

1st Example

Ac-D-NaI-D-p-Cl-Phe-D-Trp-Ser-Tyr-D-Ser(Rha)-Leu-Ser(Rha)-pro-Azagly-NH$_2$

1a. H-Ser[Rha(Ac$_3$)]-OH 55 ml of diethylamine are added to a stirred solution of 30 g (50 mmol) of Fmoc-Ser[Rha(Ac$_3$)]-OH in 150 ml of dimethylformamide. After 10 minutes, the solution is concentrated under high vacuum and the residue is triturated with MTB ether. The precipitate is filtered off with suction and washed with MTB ether. The substance is dried under high vacuum.

Yield: 17.13 g (91%) $[\alpha]_D^{26} = -31°$ (c=1, in glacial acetic acid)

1b. Fmoc-Leu-Ser[Rha(Ac$_3$)]-OH 20.4 g of Fmoc-Leu-OObt are added to a stirred suspension of 17 g (45 mmol) of H-Ser[Rha(Ac$_3$)]-OH in 100 ml of dimethylformamide at 0° C. Everything has dissolved after 1 hour. The solution is left to stand at room temperature overnight and concentrated under high vacuum. The residue is dissolved in ethyl acetate and extracted by shaking successively 3 times with saturated NaHCO$_3$ solution, water, twice with KHSO$_4$ buffer and twice with water. The ethyl acetate phase is dried over Na$_2$SO$_4$ and concentrated, and the residue is reprecipitated from diethyl ether/petroleum ether. The precipitate is again digested with petroleum ether and filtered off with suction.

Yield: 22.2 g (69%) $[\alpha]_D^{26} = -20°$ (c=1, in glacial acetic acid)

1c. Fmoc-Leu-Ser[Rha(Ac$_3$)]-Pro-Azagly-NH$_2$ 2 ml of N-ethylmorpholine and 3.5 g of DCC are added to a stirred solution of 5 g of HClO$_4$·H-Pro-Azagly-NH$_2$ (16.4 mmol), 11.7 g of Fmoc-Leu-Ser[Rha(Ac$_3$)]-OH and 2.7 g of HOObt in 60 ml of dimethylformamide at 0° C. After stirring at 0° C. for 1 hour, the mixture is placed at room temperature overnight. The next day the precipitate is filtered off with suction and the filtrate is concentrated. The residue is dissolved in ethyl acetate and washed successively with water, twice with saturated NaHCO$_3$ solution, water, twice with KHSO$_4$ buffer and water, and dried over Na$_2$SO$_4$. The solution is concentrated in vacuo, and the residue is triturated with diethyl ether.

Yield: 11.87 g (83%) $[\alpha]_D^{26} = -54.8°$ (c=1, in glacial acetic acid)

1d. H-Leu-Ser[Rha(Ac$_3$)]-Pro-AzaglY-NH$_2$ 15 ml of diethylamine are added to a stirred solution of 11.9 g (13.7 mmol) of Fmoc-Leu-Ser[Rha(Ac$_3$)]-Pro-Azagly-NH$_2$ in 90 ml of dimethylformamide at room temperature. After 10 minutes, the mixture is concentrated under high vacuum, and the residue is triturated with diethyl ether. The precipitate is filtered off with suction and washed with MTB ether.

Yield: 7.71 g (87%)

1e. Fmoc-D-Ser[Rha(Ac$_3$)]-Leu-Ser[Rha(Ac$_3$)]-Pro-Azagly-NH$_2$ 2.52 g of DCC are added to a stirred solution of 7.71 g (12 mmol) of H-Leu-Ser[Rha(Ac$_3$)]-Pro-Azagly-NH$_2$, 7.2 g of Fmoc-D-Ser[Rha(Ac$_3$)] and 1.68 g of HOBt in 60 ml of dimethylformamide at 0° C. The mixture is left to stir at 0° C. for 1 hour and to stand at room temperature overnight. Working up is carried out as in Example 1c. The substance is further purified by chromatography on silica gel in methylene chloride/acetone (9:1) and methylene chloride/methanol (9:0.5).

Yield: 11.55 g (78%)

1f. H-D-Ser[Rha(Ac$_3$)]-Leu-Ser[Rha(Ac$_3$)]-Pro-Azagly-NH$_2$ 4.2 ml of diethylamine are added to a stirred solution of 4.75 g (3.87 mmol) of Fmoc-D-Ser[Rha(Ac$_3$)]-Leu-Ser[Rha(Ac$_3$)]-Pro-Azagly-NH$_2$ in 30 ml of dimethylformamide at room temperature. After 10 minutes, the mixture is concentrated under high vacuum and the residue is triturated twice with diethyl ether.

Yield: 3.46 g (89%) $[\alpha]_D^{26} = -63°$ (c=2, in glacial acetic acid)

1g. Z-Ser(tBu)-Tyr(tBu)-OtBu 44.7 g (151.4 mmol) of Z-Ser(tBu)-OH, 49.9 g (151.3 mmol) of H-Tyr(tBu)-OtBu.HCl and 20.4 g (151.1 mmol) of HOBt are dissolved in 200 ml of dimethylformamide. 19.4 ml (151.6 mmol) of N-ethylmorpholine and 33.3 g (151.4 mmol) of DCC are added at 0° C. while stirring. The mixture is left to stir at 0° C. for 1 hour and to stand at room temperature overnight. The precipitate is filtered off with suction, and the filtrate is concentrated. The residue is dissolved in ethyl acetate and extracted successively with water, KHSO$_4$/K$_2$SO$_4$ buffer, NaHCO$_3$ solution and water, dried over Na$_2$SO$_4$ and concentrated.

Yield: 87 g of oil (100.8%)

1h. H-Ser-(tBu)-Tyr(tBu)-OtBu.HCl 2

87.3 g (153 mmol) of Z-Ser(tBu)-Tyr(tBu)-OtBu are dissolved in 600 ml of methanol, and Pd/C catalyst is added. Hydrogenation is carried out in an autotitrator with addition of methanolic hydrochloric acid at pH 4.5 and passing through hydrogen. After the hydrogenation is complete, the catalyst is filtered off with suction through kieselguhr, the filtrate is concentrated, and the residue is triturated with petroleum ether. It is filtered off with suction and dried over P$_2$O$_5$ under high vacuum.

Yield: 55.8 g (77%) $[\alpha]_D^{26} = +1.6°$ (c=1, in methanol) Melting point 109°–111° C.

1i. Fmoc-D-Trp-Ser(tBu)-Tyr(tBu)-OtBu 48.5 g (102.5 mmol) of H-Ser(tBu)-Tyr(tBu)-OtBu.HCl, 43.75 g (102.5 mmol) of Fmoc-D-Trp-OH and 13.83 g (102.4 mmol) of HOBt are dissolved in 200 ml of dimethylformamide. 13.1 ml (102.3 mmol) of N-ethylmorpholine and 22.55 g (102.5 mmol) of DCC are added at 0° C. while stirring. The mixture is left to stir at 0° C. for 1 hour and to stand at room temperature overnight. The precipitate is then filtered off with suction and the filtrate is concentrated. The residue is dissolved in ethyl acetate and extracted by shaking successively with water, KHSO$_4$/K$_2$SO$_4$ buffer, NaHCO$_3$ solution and water, dried over Na2SO4 and concentrated.

Yield: 93.0 g of oil (107%, still contains DC-urea)

1k. H-D-Trp-Ser(tBu)-Tyr(tBu)-OtBu 93.0 g (about 102 mmol) of Fmoc-D-Trp-Ser(tBu)-Tyr(tBu)-OtBu are dissolved in 500 ml of dimethylformamide. 114.5 ml of diethylamine are added to this while stirring, reaction is allowed to take place at room temperature for 10 minutes, and the mixture is concentrated under high vacuum. The residue is triturated 3 times with petroleum ether and twice with diethyl ether. The diethyl ether is removed by distillation and then partition between ethyl acetate and water is carried out. The ethyl acetate is, after drying over $Na_2SO_4$, removed by distillation, and the residue is triturated twice with diethyl ether.

Yield: 72.5 g (114%) of oil

1l. Fmoc-D-p-CI-Phe-OH 118.0 g (519 mmol) of H-D-p-CI-Phe-OH are suspended in 2000 ml of dioxane/water (1:1). 123 g of $NaHCO_3$ (1464 mmol) and 164.5 g (488 mmol) of Fmoc-ONSu are added to this. The mixture is stirred at room temperature for 5 hours and stood at this temperature overnight. The slight precipitate is filtered off with suction, the dioxane is substantially removed by distillation, the mixture is acidified (pH 2–3) with 2N HCl, and the precipitate is filtered off with suction and thoroughly washed with water. The substance is recrystallized from 5 liters of isopropanol. After standing at 4° C. for 3 hours, the precipitate is filtered off with suction and treated with petroleum ether in order to remove the isopropanol.

Yield: 167.6 g (batch 1, contains 0.76 % Fmoc-L-pCI-Phe-OH) Melting point 172°–174° C. $[\alpha]_D^{26} = +22.3°$ (c=1, in dimethylformamide)

1m. Fmoc-D-p-Cl-Phe-D-Trp-Ser(tBu)-Tyr(tBu)-OtBu 72.5 g (about 100 mmol) of H-D-Trp-Ser(tBu)-Tyr(tBu)-OtBu, 42.2 g (100 mmol) of Fmoc-D-p-CI-Phe-OH and 13.5 g (100 mmol) of HOBt are dissolved in 400 ml of dimethylformamide. 20.6 g (100 mmol) of DCC are added to this at 0° C. while stirring. The mixture is left to stir at 0° C. for 1 hour and to stand at room temperature overnight. The DC-urea is filtered off with suction, and the filtrate is concentrated. The residue is dissolved in ethyl acetate, again filtered and extracted successively with water, $NaHCO_3$ solution and water, dried over $Na_2SO_4$ and concentrated. The residue is dissolved in diethyl ether and reprecipitated amorphously with petroleum ether. The residue is dissolved in 500 ml of methanol, filtered and added dropwise to 1.5 ml of water. The crystalline precipitate is filtered off with suction and dried over $P_2O_5$ under high vacuum.

Yield: 80 g (77.8%) $[\alpha]_D^{26} = +4.9°$ (c=1, in methanol) melting point 96°–98° C.

1n. H-D-p-Cl-Phe-D-Trp-Ser(tBu)-Tyr(tBu)-OtBu 80 g (77.9 mmol) of Fmoc-D-p-Cl-Phe-D-Trp-Ser(tBu)-Tyr(tBu)-OtBu are dissolved in 600 ml of dimethylformamide. 81 ml of diethylamine are added to this at room temperature. After a reaction time of 20 minutes at room temperature, the mixture is concentrated under high vacuum, and the residue is triturated with petroleum ether. This is repeated twice. The substance is then dissolved in diethyl ether, filtered to remove insolubles and concentrated. This procedure is repeated twice.

Yield: 64.9 g of oil (104.9%)

1o. Ac-D-Nal-D-p-Cl-Phe-D-Trp-Ser(tBu)-Tyr(tBu)-OtBu 64.9 g (about 77.9 mmol) of H-D-p-Cl-Phe-D-Trp-Ser(tBu)-Tyr(tBu)-OtBu, 19.8 g (76.95 mmol) of Ac-D-Nal-OH and 12.46 g (76.4 mmol) of HOObt are dissolved in 500 ml of dimethylformamide. 16.93 g (76.95 mmol) of DCC are added at 0° C. while stirring. The mixture is left to stir at 0° C. for 1 hour and to stand at room temperature overnight. The DC-urea is then filtered off with suction, the filtrate is concentrated, and the residue is triturated with ethyl acetate. The precipitate is filtered off with suction and dried.

Yield: 47.9 g (59%) Melting point 224°–228° C. with decomposition $[\alpha]_D^{26} = -12.6°$ (c=1, in 90% strength acetic acid)

1p. Ac-D-Nal-D-p-Cl-Phe-D-Trp-Ser-Tyr-OH 47.6 g (45.6 mmol) of Ac-D-Nal-D-p-Cl-Phe-D-Trp-Ser(tBu)-Tyr(tBu)-OtBu in a mixture of 350 ml of 90% strength aqueous trifluoroacetic acid and 35 ml of 1,2-dimercaptoethane are concentrated at room temperature, and the residue is triturated with diethyl ether and filtered off with suction. The substance is further purified by dissolving in hot isopropanol and precipitating with petroleum ether.

Yield: 33.67 g Melting point 196° C. with decomposition (sinters above 159° C.), $[\alpha]_D^{26} = -3.5°$ (c=1, in methanol)

1q. Ac-D-Nal-D-p-Cl-Phe-D-TrP-Ser-TYr-D-Ser[-Rha(Ac$_3$)]-Leu-Ser[Rha(Ac$_3$)]-Pro-Azagly-NH$_2$ 210 mg of DCC are added to a stirred solution of 1 g (1 mmol) of H-D-Ser[Rha(Ac$_3$)]-Leu-Ser[Rha(Ac$_3$)]-Pro-Azagly-NH$_2$, 875 mg of Ac-D-Nal-D-p-Cl-Phe-D-Ser-Tyr-OH and 163 mg of HOObt in 4 ml of dimethylformamide at 0° C. After one hour at 0° C., the mixture is left to stand at room temperature overnight. The next day the precipitate is filtered off with suction and the filtrate is concentrated. The residue is concentrated and triturated with MTB ether. The crude substance is chromatographed on silica gel in methylene chloride/methanol/acetic acid/water (9:1:0.1:0.1 ).

Yield: 1.09 g (59%) $[\alpha]_D^{26} = -48.5°$ (c=1, in glacial acetic acid)

1r. Ac-D-Nal-D-p-Cl-Phe-D-Trp-Ser-Tyr-D-Ser(-Rha)-Leu-Ser(Rha)-Pro-Azagly-NH$_2$ 360 mg of $K_2CO_3$ are added to a stirred solution of 400 mg (0.21 mmol) of Ac-D-Nal-D-p-Cl-Phe-D-Trp-Ser-Tyr-D-Ser[Rha(Ac$_3$)]-Leu-Ser[Rha(Ac$_3$)]-Pro-Azagly-NH$_2$ in 4 ml of 90% strength aqueous methanol at room temperature. The mixture is stirred for 10 minutes, acidified with KHSO$_4$ buffer and extracted twice with n-pentanol. The combined n-pentanol phases are concentrated and purified by chromatography on silica gel in n-butanol/glacial acetic acid/water (63:9.5:27.5).

Yield: 112 mg (27%) $[\alpha]_D^{26} = -38.2°$ (c=1, in glacial acetic acid)

2ND EXAMPLE

Ac-D-Nal-D-p-Cl-Phe-D-Pal-Ser-Tyr-D-Ser(Rha)-Leu-Ser (Rha)-Pro-Azagly-NH$_2$

2a. Fmoc-D-Pal-Ser(tBu)-Tyr(tBu)-OtBu 1.3 ml of ethylmorpholine and 2.2 g of DCC are added to a stirred solution of 3.88 g of Fmoc-D-Pal-OH (10 mmol), 4.73 g of HCl.H-Ser(tBu)-Tyr(tBu)-OtBu and 1.35 g of HOBt in 40 ml of dimethylformamide at 0° C. The mixture is stirred at 0° C. for 1 hour and left to stand at room temperature overnight. The precipitate is filtered off with suction and the residue is dissolved in ethyl acetate. The solution is extracted successively with water, saturated NaHCO$_3$ solution, KHSO$_4$ buffer and water, dried over sodium sulfate and concentrated.

Yield: 3.74 g (46.3%), Melting point 86°–88° C. $[\alpha]_D^{23} = +10.1°$ (c=1, in MeOH)

2b. H-D-Pal-Ser(tBu)-Tyr(tBu)-OtBu 4.8 ml of diethylamine are added to a solution of 3.74 g of Fmoc-D-Pal-Ser(tBu)-OtBu in 20 ml of dimethylformamide at room temperature. After 10 minutes, the mixture is concentrated and the residue is successively triturated twice with petroleum ether and dissolved in diethyl ether. The resulting precipitate is filtered off with suction and the diethyl ether solution is concentrated.

Yield: 2.7 g of oil

2c. Fmoc-D-p-Cl-Phe-D-Pal-Ser(tBu)-Tyr(tBu)-OtBu 1.02 g of DCC are added to a stirred solution of the above 2.7 g of H-D-Pal-Ser(tBu)-Tyr(tBu)-OtBu, 2.16 g of Fmoc-p-Cl-D-Phe-OH and 0.62 g of HOBt in 30 ml of dimethylformamide at 0° C. The mixture is left to stir at 0° C. for 1 hour and to stand at room temperature overnight. The precipitate is filtered off with suction, and the filtrate is concentrated, and the residue is worked up as in Example 2a. The residue is reprecipitated from diethyl ether/petroleum ether.

Yield 3.25 g Melting point 98°–102° C. $[\alpha]_D^{23} = +12.0°$ (c=1, in MeOH)

2d. H-D-p-Cl-Phe-D-Pal-Ser(tBu)-Tyr(tBu)-OtBu 3.0 g of Fmoc-D-p-Cl-Phe-D-Pal-Ser(tBu)-Tyr(tBu)-OtBu are reacted with 3.1 ml of diethylamine in 50 ml of dimethylformamide as in Example 2b.

Yield 1.6 g of oil

2e. Ac-D-Nal-D-p-Cl-Phe-D-Pal-Ser(tBu)-Tyr(tBu)-OtBu 0.43 g of DCC is added to a stirred solution of the above 1.6 g of H-D-p-Cl-Phe-D-Pal-Ser-(tBu)-Tyr(-tBu)-OtBu, 0.5 g of Ac-D-Nal-OH and 0.32 g of HOObt in 20 ml of dimethylformamide at 0° C. The mixture is left to stir at 0° C. for 1 hour and to stand at room temperature overnight. The precipitate is filtered off with suction and the filtrate is concentrated. The residue is triturated with ethyl acetate and then filtered off with suction.

Yield 1.43 g Melting point 208°–210° C. $[\alpha]_D^{23} = 7.0°$ (c=1, in glacial acetic acid)

2f. Ac-D-Nal-D-p-Cl-Phe-D-Pal-Ser-Tyr-OH-trifluoroacetate 1.4 g (1.39 mmol) of Ac-D-Nal-D-p-Cl-Phe-D-Pal-Ser(tBu)-Tyr(tBu)-OtBu are introduced into a mixture of 15 ml of 90% strength aqueous trifluoroacetic acid and 1.5 ml of 1,2-dimercaptoethane. The mixture is left to stand at room temperature for 1 hour and is concentrated. The residue is triturated with diethyl ether and filtered off with suction.

Yield 1.1 g Melting point 264° C. (with decomposition) 2g. Ac-D-Nal-D-p-Cl-Phe-D-Pal-Ser-Tyr-D-Ser[-Rha(Ac$_3$)]-Leu-Ser[Rha(Ac$_3$)]-Pro-Azagly-NH$_2$ 0.13 ml of N-ethylmorpholine and 210 mg of DCC are added to a solution of 1 g (1 mmol) of H-D-Ser[-Rha(Ac$_3$)]-Leu-Ser[Rha(Ac$_3$)]-Pro-Azagly-NH$_2$, 838 mg of Ac-D-Nal-D-pCl-Phe-D-Pal-Ser-Tyr-OH trifluoroacetate and 163 mg of HOObt in 4 ml of dimethylformamide. Mixture and working up as in Example 1q but without column purification.

Yield of crude substance: 1.55 g (85%)

2h. Ac-D-Nal-D-p-Cl-Phe-D-Pal-Ser-Tyr-D-Ser(-Rha)-Leu-Ser(Rha)-Pro-AzaglY-NH$_2$ 1.4 g of K$_2$CO$_3$ are added to a stirred solution of 1.5 g (0.8 mmol) of the crude Ac-D-Nal-D-p-Cl-Phe-D-Pal-Ser-Tyr-D-Ser[Rha(Ac$_3$)]-Leu-Ser[Rha(Ac$_3$)]-Pro-Azagly-NH$_2$ in 15 ml of 90% strength aqueous methanol at room temperature. Working up is carried out as in Example 1r.

The crude material is chromatographed on silica gel in methylene chloride/methanol/water/acetic acid (20:4:1.5:5) and methanol/water/acetic acid (1:1:1).

Yield 270 mg (22%) $[\alpha]_d^{26} = -45°$ (c=1, in glacial acetic acid)

EXAMPLE 3

Ac-D-Nal-D-p-Cl-Phe-D-Trp-Ser-Tyr-D-Ser(Rha)-Leu-Ser(Xyl)-Pro-Azagly-NH$_2$

3a. H-Ser[Xyl(Ac$_3$)]-OH 16.37 g of Fmoc-Ser[Xyl(Ac$_3$)]-OH in 100 ml of dimethylformamide are reacted with 30.8 ml of dimethylamine in analogy to Example 1a.

Yield 9.65 g (95%)

3b. Fmoc-Leu-Ser[Xyl(Ac$_3$)]-OH 9.65 g (26.65 mmol) of H-Ser[Xyl(Ac$_3$)]-OH are reacted with 12 g of Fmoc-Leu-OObt in 70 ml of dimethylformamide in analogy to Example 1b.

Yield 12.8 g (69%)

3c. Fmoc-Leu-Ser[Xyl(Ac$_3$)]-Pro-Azagly-NH$_2$ 12.8 g (18.65 mmol) of Fmoc-Leu-Ser[Xyl(Ac$_3$)]-OH are reacted with 5.7 g of HClO$_4$.H-Pro-Azagly-NH$_2$, 3.04 g of HOObt, 2.36 ml of N-ethylmorpholine and 3.91 g of DCC in analogy to Example 1c.

Yield 11.6 g (73%)

3d. H-Leu-Ser[Xyl(Ac$_3$)]-Pro-Azagly-NH$_2$ 11.6 g (13.8 mmol) of Fmoc-Leu-Ser[Xyl(Ac$_3$)]-Pro-Azagly-NH$_2$ are reacted with 15.2 ml of diethylamine in 100 ml of dimethylformamide in analogy to Example 1d.

Yield 7.47 g (86%)

3e. Fmoc-D-Ser[Rha(Ac$_3$)]-Leu-Ser[Xyl(Ac$_3$)]-Pro-Azagly-NH$_2$ 7.47 g of H-Leu-Ser[Xyl(Ac$_3$)]-Pro-Azagly-NH$_2$ are reacted with 7.25 g of Fmoc-D-Ser[Rha(Ac$_3$)]OH, 1.7 g of HOBt and 2.54 g of DCC in analogy to Example 1e.

Yield 10.48 g (71%) $[\alpha]_D^{26} = -57°$ (c=1, in glacial acetic acid)

3f. H-D-Ser[Rha(AC$_3$)]-Leu-Ser[Xyl(Acs)]-Pro-Azagly-NH$_2$ 2 g (1.65 mmol) of Fmoc-D-Ser[Rha(Ac$_3$)]-Leu-Ser[Xyl(Ac$_3$)]-Pro-Azagly-NH$_2$ are reacted with 1.8 ml of diethylamine in 15 ml of dimethylformamide in analogy to Example 1f.

Yield 1.47 g (90%) $[\alpha]_D^{26} = -68°$ (c=1, in glacial acetic acid)

3g. Ac-D-Nal-D-p-Cl-Phe-D-Trp-Ser-Tyr-D-Ser(-Rha)-Leu-Ser(Xyl)-Pro-Azagly-NH$_2$ 990 mg (1 mmol) of H-D-Ser[Rha(Ac$_3$)]-Leu-Ser[Xyl(Ac$_3$)-Pro-Azagly-NH$_2$ are reacted with 875 mg of Ac-D-Nal-D-p-Cl-Phe-D-Trp-Ser-Tyr-OH, 163 mg of HOObt and 210 mg of DCC in analogy to Example 1q.

Yield 1.07 g (59%) $[\alpha]_d^{26} = -45°$ (c=1, in glacial acetic acid)

3h. Ac-D-Nal-D-p-Cl-Phe-D-Trp-Ser-Tyr-D-Ser(-Rha)-Leu-Ser(Xyl)-Pro-Azagly-NH$_2$ 560 mg (0.3 mmol) of Ac-D-Nal-D-p-Cl-Phe-D-Trp-Ser-Tyr-D-Ser[Rha(Ac$_3$)]-Leu-Ser[Xyl(Ac$_3$)]-Pro-Azagly-NH$_2$ are reacted with 497 mg of K$_2$CO$_3$ in 5 ml of 90% strength aqueous methanol in analogy to Example 1r.

Yield 80 mg (26%) $[\alpha]_D^{26} = -39°$ (c=1, in glacial acetic acid)

EXAMPLE 4

Ac-D-Nal-D-p-Cl-Phe-D-Pal-Ser-Tyr-D-Ser(Rha)-Leu-Ser(Fuc)-Pro-Azagly-NH$_2$

4a. H-Ser[Fuc(Aca)]-OH 11.82 g (19.73 mmol) of Fmoc-Ser[Fuc(Aca)]-OH are reacted with 21.7 ml of diethylamine in 50 ml of dimethylformamide in analogy to Example 1a.

Yield 7.08 g (95%)

4b. Fmoc-Leu-Ser[Fuc(Ac₃)]-OH 7.08 g (18.78 mmol) of H-Ser[Fuc(Ac₃)]-OH are reacted with 8.41 g of Fmoc-Leu-OObt in 100 ml of dimethylformamide in analogy to Example 1b.

Yield 8.23 g (68%)

4c. Fmoc-Leu-Ser[Fuc(Ac₃)]-Pro-Azagly-NH₂

8.2 g (11.51 mmol) of Fmoc-Leu-Ser[Fuc(Ac₃)]-OH are reacted with 3.5 g of HClO₄.H-Pro-Azagly-NH₂, 1.88 g of HOObt, 1.46 ml of N-ethylmorpholine and 2.42 g of DCC in 60 ml of dimethylformamide in analogy to Example 1c.

Yield 6.87 g (69%)

4d. H-Leu-Ser[Fuc(Ac₃)]-Pro-Azagly-NH₂

6.87 g (7.93 mmol) of Fmoc-Leu-Ser[Fuc(Ac₃)]-Pro-Azagly-NH₂ are reacted with 8.7 ml of diethylamine in 50 ml of dimethylformamide in analogy to Example 1d.

Yield 4.49 g (88%)

4e. Fmoc-D-Ser[Rha(Ac₃)]-Leu-Ser[Fuc(Ac₃)]-Pro-Azagly-NH₂

4.49 g (6.97 mmol) of H-Leu-Ser(Fuc)-Pro-Azagly-NH₂ are reacted with 4.18 g of Fmoc-D-Ser[Rha(Ac₃)]-OH, 976 mg of HOBt and 1.47 g of DCC in 40 ml of dimethylformamide in analogy to Example 1e.

Yield 6.64 g (77%) $[\alpha]_D^{26} = -23.3°$ (c=1, in glacial acetic acid)

4f. H-D-Ser[Rha(Ac₃)]-Leu-Ser[Fuc(Ac₃)]-Pro-Azagly-NH₂

6.6 g (5.38 mmol) of Fmoc-D-Ser[Rha(Ac₃)]-Leu-Ser[Fuc(Ac₃)]Pro-Azagly-NH₂ are reacted with 6 ml of diethylamine in 20 ml of dimethylformamide in analogy to Example 1f.

Yield 4.82 g (90%) $[\alpha]_D^{26} = -45°$ (c=1, in glacial acetic acid)

4g. Ac-D-Nal-D-p-Cl-Phe-D-Pal-Ser-Tyr-D-Ser[Rha(Ac₃)]-Leu-Ser[Fuc(Acs)]-Pro-Azagly-NH₂

1 g (1 mmol) of H-D-Ser[Rha(Ac₃)]-Leu-Ser[Fuc(Ac₃)]-Pro-Azagly-NH₂ are reacted with 838 mg of Ac-D-Nal-D-p-Cl-Phe-D-Pal-Ser-Tyr-OH trifluoroacetate, 0.13 ml of N-ethylmorpholine, 163 mg of HOObt and 210 mg of DCC in 4 ml of dimethylformamide in analogy to Example 2g.

Yield 1.35 g (74%)

4h. Ac-D-Nal-D-p-Cl-Phe-D-Pal-Ser-Tyr-D-Ser(-Rha)-Leu-Ser(Fuc)-Pro-Azagly-NH₂

1.35 g of Ac-D-Nal-D-p-Cl-Phe-D-Pal-Ser-Tyr-D-Ser[Rha(Ac₃)]-Leu-Ser[Fuc(Ac₃)]-Pro-Azagly-NH₂ are reacted with 1.24 g of K₂CO₃ in 15 ml of 90% strength methanol in analogy to Example 2h.

Yield 170 mg (15%) $[\alpha]_D^{26} = -17.3°$ (c=1, in glacial acetic acid)

EXAMPLE 5

Ac-D-Nal-D-p-Cl-Phe-D-Pal-Ser-Tyr-D-Ser(Rha)-Leu-Ser(Rha)-Pro-D-Ala-NH₂

5a. Fmoc-Pro-D-Ala-NH₂

3.36 g of DCC are added to a stirred solution of 5.4 g (16 mmol) of Fmoc-Pro-OH, 2 g of HCl.H-D-Ala-NH₂ and 2.24 g of HOBt in 30 ml of dimethylformamide at 0° C. The mixture is left to stir at 0° C. for 1 hour and to stand at room temperature overnight. The precipitate is filtered off with suction and the filtrate is concentrated. The residue is dissolved in ethyl acetate and extracted by shaking successively with water, twice with saturated NaHCO₃ solution, water, KHSO₄ buffer and water. Fmoc-Pro-D-Ala-NH₂ precipitates in the ethyl acetate phase during this and is filtered off with suction. The ethyl acetate mother liquor is concentrated and triturated with diethyl ether and filtered with suction.

Combined yield: 5.76 g (88%) $[\alpha]_D^{26} = -29°$ (c=1, in ethyl acetate)

5b. H-Pro-D-Ala-NH₂

15.3 ml of diethylamine are added to a solution of 5.66 g (13.9 mmol) of Fmoc-Pro-D-Ala-NM₂ in 30 ml of dimethylformamide at room temperature. After 6 minutes, the solution is concentrated under high vacuum. The residue is triturated with diethyl ether.

Yield 2.47 g (96%)

5c. Fmoc-Leu-Ser[Rha(Ac₃)]-Pro-D-Ala-NH₂

2.8 g of DCC are added to a stirred solution of 9.5 g (13.35 mmol) of Fmoc-Leu-Ser[Rha(Ac₃)]-OH, 2.4 g of H-Pro-D-Ala-NH₂ and 2.17 g of HOObt at 0° C. The mixture is left to stir at 0° C. for 1 hour and to stand at room temperature overnight. The precipitate is filtered off with suction and the filtrate is concentrated. The residue is dissolved in a mixture of ethyl acetate and pentanol (10:2) and washed successively with water, twice with saturated NaHCO₃ solution, water, KHSO₄ buffer and water. The organic phase is dried over Na₂SO₄ and concentrated. The residue is precipitated from diethyl ether/petroleum ether and filtered off with suction.

Yield 7.75 g (66%) $[\alpha]_D^{26} = -38°$ (c=1, in glacial acetic acid)

5d. H-Leu-Ser[Rha(Ac₃)]-Pro-D-Ala-NH₂

7.7 g of Fmoc-Leu-Ser[Rha(Ac₃)]-Pro-D-Ala-NH₂ are reacted with 9.7 ml of diethylamine in 30 ml of dimethylformamide in analogy to Example 1 d.

Yield 5.25 g (90%)

5e. Fmoc-D-Ser[Rha(Ac₃)]-Leu-Ser[Rha(Ac₃)]-Pro-D-Ala-NH₂

5.2 g (8.8 mmol) of Fmoc-D-Ser[Rha(Ac₃)]-OH are reacted with 5.25 g of H-Leu-Ser-[Rha(Ac₃)]-Pro-D-Ala-NH₂, 1.23 g of HOBt and 1.84 g of DCC in 50 ml of dimethylformamide in analogy to Example 1e.

Yield 8.01 g (73%) $[\alpha]_D^{26} = -43.3°$ (c=1, in glacial acetic acid)

5f. H-D-Ser[Rha(Ac₃)]-Leu-Ser[Rha(Ac₃)]-Pro-D-Ala-NH₂

4 g (3.23 mmol) of Fmoc-D-Ser[Rha(Ac₃)]-Leu-Ser[Rha(Ac₃)]-Pro-D-Ala-NH₂ are reacted with 3.6 ml of diethylamine in 10 ml of dimethylformamide in analogy to Example 1f.

Yield 2.98 g (91%) $[\alpha]_D^{26} = -49°$ (c=1, in glacial acetic acid)

5g. Ac-D-Nal-D-p-Cl-Phe-D-Pal-Ser-Tyr-D-Ser[Rha(Ac₃)]-Leu-Ser[Rha(Ac₃)]-Pro-D-Ala-NH₂

838 mg (1 mmol) of Ac-D-Nal-D-p-Cl-Phe-D-Pal-Ser-Tyr-OH trifluoroacetate are reacted with 1 g of H-D-Ser[Rha(Ac₃)]-Leu-Ser[Rha(Ac₃)]-Pro-D-Ala-NH₂, 163 mg of HOObt, 0.13 ml of N-ethylmorpholine and 210 mg of DCC in 9 ml of dimethylformamide in analogy to Example 2g.

Yield 1.36 g (74%) $[\alpha]_D^{26} = -25°$ (c=1, in glacial acetic acid)

5h. Ac-D-Nal-D-p-Cl-Phe-D-Pal-Ser-TYr-D-Ser(-Rha)-Leu-Ser(Rha)-Pro-D-Ala-NH₂

1.34 g (0.74 mmol) of Ac-D-Nal-D-p-Cl-Phe-D-Pal-Ser-Tyr-D-Ser[Rha(Ac₃)]-Leu-Ser[Rha(Ac₃)]-Pro-D-Ala-NH₂ are reacted with 1.24 g of K₂CO₃ in 15 ml of 90% strength aqueous methanol in analogy to Example 2h.

Yield 230 mg (20%) $[\alpha]_D^{26} = -36°$ (c=1, in glacial acetic acid)

We claim:

1. A peptide of the formula I $$X-A-B-C-Ser-D-E-F-G-Pro-H \quad (I)$$
$$\phantom{X-}1\phantom{-}2\phantom{-}3\phantom{-}4\phantom{---}5\phantom{---}6-7-8-9-10\phantom{-}$$

in which

X is $C_2$-$C_8$-alkanoyl;

A is D-Nal (2), D-Phe or D-Trp, where the aromatic ring can optionally be substituted by one or two identical or different radicals selected from the group consisting of bromine, chlorine, fluorine, nitro, $C_1$-$C_4$-alkyl and $C_1$-$C_4$-alkoxy;

B is D-Phe which can optionally be substituted by one or two identical or different radicals selected from the group consisting of bromine, chlorine, fluorine, nitro, $C_1$-$C_4$-alkyl, and $C_1$-$C_4$-alkoxy;

C is D-Pal (3), D-Phe, or D-Trp, wherein the aromatic ring of D-Phe and D-Trp can optionally be substituted by one or two identical or different radicals selected from the group consisting of bromine, chlorine, fluorine, nitro, $C_1$-$C_4$-alkyl, and $C_1$-$C_4$-alkoxy;

D is Tyr or His;

E is D-Ser($R^1$);

F is Leu, Trp or Phe;

G is L-Ser($R^1$) having a non-basic charge;

H is Gly-$NH_2$, D-Ala-$NH_2$, or Azagly-$NH_2$;

$R^1$ is a glycosyl radical; or the physiologically tolerated salt thereof.

2. A peptide of the formula I as claimed in claim 1, in which

X is acetyl;

A is D-Nal(2);

B is D-Phe(p-Cl);

C is D-Pal(3) or D-Trp;

D is Tyr;

E is D-Ser($R^1$);

F is Leu;

G is L-Ser($R^1$) having a non-basic charge; H is D-Ala-$NH_2$ or Azagly-$NH_2$, and the physiologically acceptable salt thereof.

3. A pharmaceutical composition comprising a peptide of the formula I as claimed in claim 1 or the physiologically acceptable salt thereof and a pharmaceutically acceptable carrier.

4. A method of lowering plasma gonadotropin, testosterone, and estrogen in a mammal comprising administering to said mammal an effective amount of a peptide of the formula I as claimed in claim 1 or a pharmaceutically acceptable salt thereof.

* * * * *

UNITED STATES PATENT AND TRADEMARK OFFICE
CERTIFICATE OF CORRECTION

PATENT NO. : 5,434,138
DATED : July 18, 1995
INVENTOR(S) : Wolfgang KONIG et al

It is certified that error appears in the above-indentified patent and that said Letters Patent is hereby corrected as shown below:

Claim 1, Column 17, Line 18, "D-Phe or D-Trp, where" should read --D-Phe, or D-Trp, wherein--.

Claim 1, Column 18, Lines 11-12, "physiologically tolerated" should read --pharmaceutically acceptable--.

Claim 2, Column 18, Line 23, "physiologically" should read --pharmaceutically--.

Signed and Sealed this

Twenty-sixth Day of December, 1995

Attest:

BRUCE LEHMAN

*Attesting Officer*   *Commissioner of Patents and Trademarks*